United States Patent [19]

Huang et al.

[11] Patent Number: 5,043,164
[45] Date of Patent: Aug. 27, 1991

[54] BLOOD-STABLE, CHOLESTEROL-FREE LIPOSOMES

[75] Inventors: Leaf Huang; Dexi Liu, both of Knoxville, Tenn.

[73] Assignee: The University of Tennessee Research Corporation, Knoxville, Tenn.

[21] Appl. No.: 298,452

[22] Filed: Jan. 17, 1989

[51] Int. Cl.$^5$ .................. A61K 9/133; B01J 13/02
[52] U.S. Cl. ............................ 424/423; 264/4.1; 264/4.6; 428/402.2; 424/450; 436/829; 514/970; 514/971
[58] Field of Search .............. 424/450, 423; 436/829; 264/4.1, 4.3, 4.6; 428/402.21, 402.22; 514/970, 971

[56] References Cited

U.S. PATENT DOCUMENTS

| | | | |
|---|---|---|---|
| 4,708,933 | 11/1987 | Huang | 436/829 X |
| 4,789,633 | 12/1988 | Huang | 424/450 X |
| 4,861,597 | 8/1989 | Kida et al. | 424/450 |
| 4,915,951 | 4/1990 | Baldeschweiler et al. | 424/450 |
| 4,920,016 | 4/1990 | Allen et al. | 424/450 |
| 4,925,661 | 5/1990 | Huang | 424/450 X |

FOREIGN PATENT DOCUMENTS 155109  8/1985  Japan ................................ 424/450

OTHER PUBLICATIONS

Chem. Abs., vol. 107, No. 3, Abs. No. 19734s, Leventis et al. "pH-Dependent Stability and Fusion of Liposomes" . . . , 1987.
Chem. Abs., vol. 111, No. 12, Abs. No. 102625k, Liu et al., "Characterization of Plasma Stabilized Liposomes . . . ", 1989.
Chem. Abs., vol. 111, No. 16, Abs. No. 140312p, Liu et al., "Small, but not Large, Unilamellar Liposomes . . . ", 1989.
Chem. Abs., vol. 112, No. 19, Abs. No. 174,393b, Liu et al., "Interactions of Serum Proteins . . . ", 1990.
Chem. Abs., vol. 112, No. 20, Abs. No. 185718n, Liu et al., "pH-Sensitive, Plasma-Stable Liposomes . . . ", 1990.
Liu et al., "Small, but not Large, Unilamellar Liposomes," *Biochemistry* 28(19) 7700-7707 (1989).
Gregoriadis et al., "The Phospholipid Component of Small Unilamellar Liposomes . . . ", Febs Letter, 119(1) 43-46 (1980).
Lelkes, P. I. et al., "Studies . . . on the Mechanism of Liposome Stabilization by Red Blood Cells In Vitro"; *Biochim. Biophys. Acta* vol. 716 (1982); pp. 410-419.
Lelkes, P. I. et al., "Stabilization of Large Multilamellar Liposomes by Human Serum In Vitro"; *Biochim. Biophys. Acta* vol. 775 (1984) pp. 395-401.

*Primary Examiner*—Richard D. Lovering
*Assistant Examiner*—John M. Covert
*Attorney, Agent, or Firm*—Ernest V. Linek; George W. Neuner

[57] ABSTRACT

Small unilamellar liposomes (d < 600 nm) comprising an unsaturated phosphatidylethanolamine (PE) such as dioleoyl PE (DOPE) and a fatty acid such as oleic acid (OA) are stabilized by adding to a freshly prepared liposome suspension, an amphipile which has a high tendency to form micelles. Examples are shown for the following micelle-forming amphiphiles: lysophospholipide, gangliosides ($GM_1$ and GTlb), sulfatide, synthetic glycopholipids such as sialo-lactosyl phosphatidylethanolamine, liopohilic drugs such as cytosine arabinoside diphosphate diacyglycerol, and proteins such as cytochrome $b_5$, human high density lipoprotein (HDL), and human glycophorin A. The stabilized liposomes are resistant to the lytic action of albumin, the major blood component which causes the lysis of this type of liposome. Prior to the present invention, liposomes comprising PE and OA were typically stabilized by the incorporation of cholesterol.

22 Claims, 3 Drawing Sheets

BLOOD-STABLE, CHOLESTEROL-FREE LIPOSOMES

BACKGROUND OF THE INVENTION

Liposomes have been extensively tested in experimental animals and in humans as a carrier for drugs and nucleic acids. One concern in this use of liposomes is the stability of the liposome during storage and the stability in the blood. The former often limits the clinical use of the liposome and the latter determines the carrier potential of the liposome.

It is well known that liposomes composed of phosphatidylcholine (PC) as the major matrix lipids are generally stable in a simple buffer upon storage and this type of liposome is widely used by many investigators. However, PC-based liposomes rapidly release the entrapped contents upon exposure to serum or plasma, unless cholesterol is included as one of the major lipid components.

Liposomes composed of phosphatidylethanolamine (PE), particularly an unsaturated PE such as dioleoyl PE (DOPE), as the major lipid component have become increasingly important for liposomal drug delivery in recent years. The equilibrium phase of DOPE at physiological temperature and pH is the hexagonal $H_{II}$ phase. However, the bilayer phase, in the form of liposomes, can be prepared by mixing DOPE with at least one other amphiphile (lipid or protein). These liposomes are generally less stable than the PC-based liposomes upon storage, due to the tendency to revert to the $H_{II}$ phase. Indeed, special conditions such as acidic pH, or binding with target cells, often trigger a rapid destabilization of the liposomes, making the liposomes suitable for intracellular drug delivery. See, for example Huang et al., U.S. Pat, No. 4,789,633, the disclosure of which is hereby incorporated herein by reference.

Thus, DOPE liposomes stabilized with weakly acidic amphiphiles such as fatty acids, acyl amino acids, and other double-chain lipids, are useful for efficient cytoplasmic delivery of drugs. DOPE liposomes stabilized with acylated antibody, known as target-sensitive immunoliposome, are useful for target-cell surface drug delivery and in vitro diagnosis of virus. See, for example Huang et al., U.S Pat. No. 4,708,933, the disclosure of which is hereby incorporated herein by reference.

At least one such liposome preparation, i.e., large unilamellar liposomes composed of DOPE and oleic acid (OA) (8:2), is not stable in serum, rapid liposome aggregation and content leakage take place within minutes after exposure to serum. Inclusion of cholesterol in such liposomes also improves the liposome stability in serum. Thus, the behavior of the large unilamellar liposomes composed of primarily DOPE is similar to those composed of primarily PC.

SUMMARY OF THE INVENTION

The present invention is based upon the observation that small, unilamellar liposomes of the lipid composition DOPE and OA, though quite unstable in buffer, become rapidly stabilized upon exposure to plasma or serum. It has also been discovered that the plasma stabilization of these liposomes depends on the liposome size. Only small liposomes (those less than about 600 nm in average diameter) are stabilized; larger liposomes are not stable in plasma.

As used herein, small liposomes are liposomes having an average diameter of less than about 600 nm, preferably less than about 300 nm, and most preferably less than about 150 nm. Large liposomes have an average diameter greater than about 600 nm. Average diameter may be determined by conventional methods well known to those of ordinary skill in this art.

In connection with the search for blood component(s) responsible for this liposome stabilization, there was also discovered a new method for preparing small unilamellar liposomes, containing no cholesterol, which are stable upon storage in buffer, yet are also stable in the blood. This new type of liposome will have a high potential to be an effective drug carrier.

Thus, one aspect of the present invention is directed to small unilamellar liposomes composed of an unsaturated phosphatidylethanolamine (PE) such as dioleoyl PE (DOPE) and a fatty acid such as oleic acid (OA), which are typically not stable at neutral pH and 37° C. In fact, if left untreated, continuous aggregation, fusion and content leakage of the liposomes are observed. However, freshly prepared liposomes can be stabilized by adding to the liposome suspension a stabilizing amount of an amphiphile which has a high tendency to form micelles. As used herein, "freshly prepared" means liposomes that are treated within up to about five (5) hours after preparation, preferably within up to about three (3) hours after preparation, and most preferably within up to about one (1) hour after preparation. Specific examples of useful stabilizing amphiphiles are; lysophospholipids, gangliosides ($GM_1$ and GTlb), sulfatide, synthetic glycopholipids such as sialo-lactosyl phosphatidylethanolamine, lipophilic drugs such as cytosine arabinoside diphosphate diacyglycerol, and proteins such as cytochrome $b_5$, human high density lipoprotein (HDL), and human glycophorin A.

The stabilized liposomes are resistant to the lytic action of albumin, the major blood component which causes the lysis of this type of liposome by extracting the fatty acid from the liposome. These liposomes are also stable over longer storage periods and under more harsh storage conditions (e.g., higher temperature), than are unstabilized liposomes of the same composition.

Thus, as used herein, the term "stabilizing amount" refers to that amount of stabilizing amphiphile which must be added to the liposome composition in order to stabilize that composition against the lytic action of albumin. The skilled artisan will appreciate that the "stabilizing amount" of different stabilizing amphiphiles will vary, but that the determination of any particular amphiphile's "stabilizing amount" may readily be conducted by routine experimentation as set forth herein.

The cholesterol-free, blood-stable liposomes of the present invention thus comprise an unsaturated phosphatidylethanolamine and a fatty acid as their major components. After liposome formation, the freshly prepared suspension of small, unilamellar liposomes is treated with a stabilizing amount of a micelle-forming amphiphile. This amphiphile is incorporated into the liposome structure and acts to prevent disruption thereof. These stabilized liposomes show a high potential to be an effective drug carrier.

Figure 2:
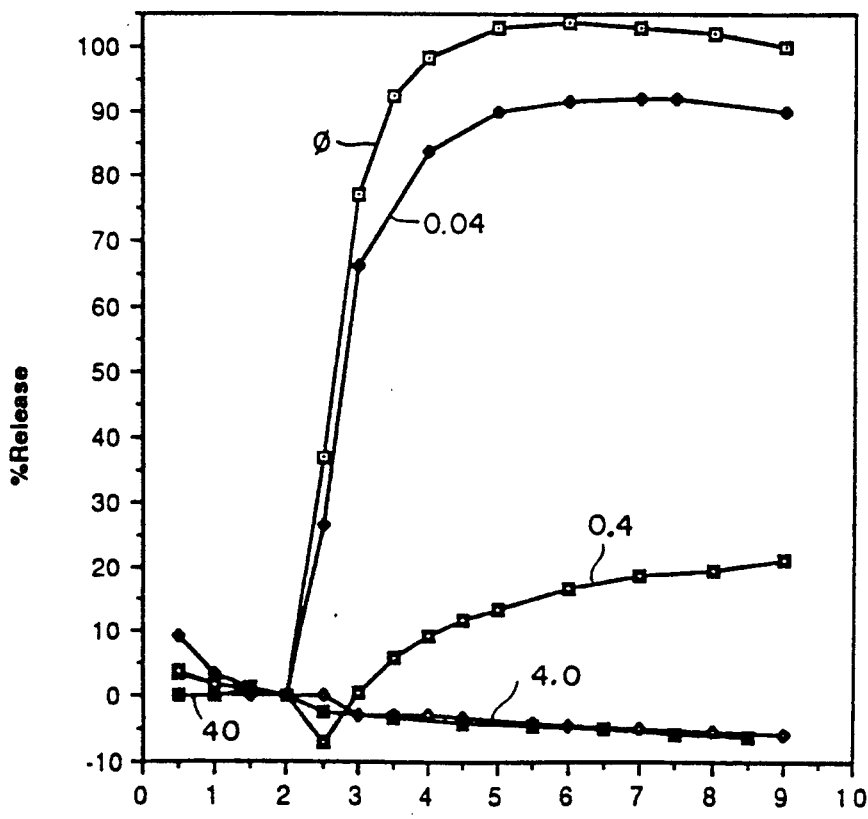

FIG. 2 illustrates the rate of release of entrapped calcein for small unilamellar liposomes (diameter=133 nm) composed of DOPE:OA were incubated at 37° C. for 15 min. with $GM_1$ at 0, 0.04, 0.4, 4, and 40 ug/ml concentration. An aliquot of the incubation mixture was then tested for calcein release with time. BSA (0.44 mg/ml) was added at 2 min.

Figure 3:
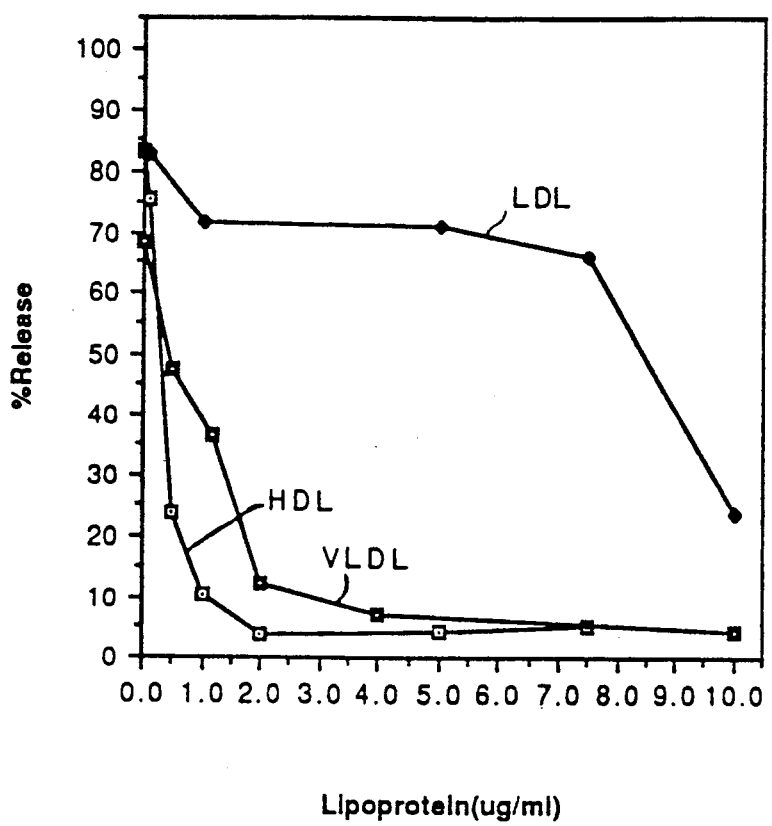

FIG. 3 demonstrates the stabilization of small unilamellar liposomes (d 100 nm) composed of DOPE:OA by human lipoproteins. Liposomes were incubated with a mixture of BSA (0.5 mg/ml) and various concentrations of lipoprotein (HDL, VLDL and LDL) for 9 min. at 37° C., and then measured for the release of the entrapped calcein.

Figure 4:
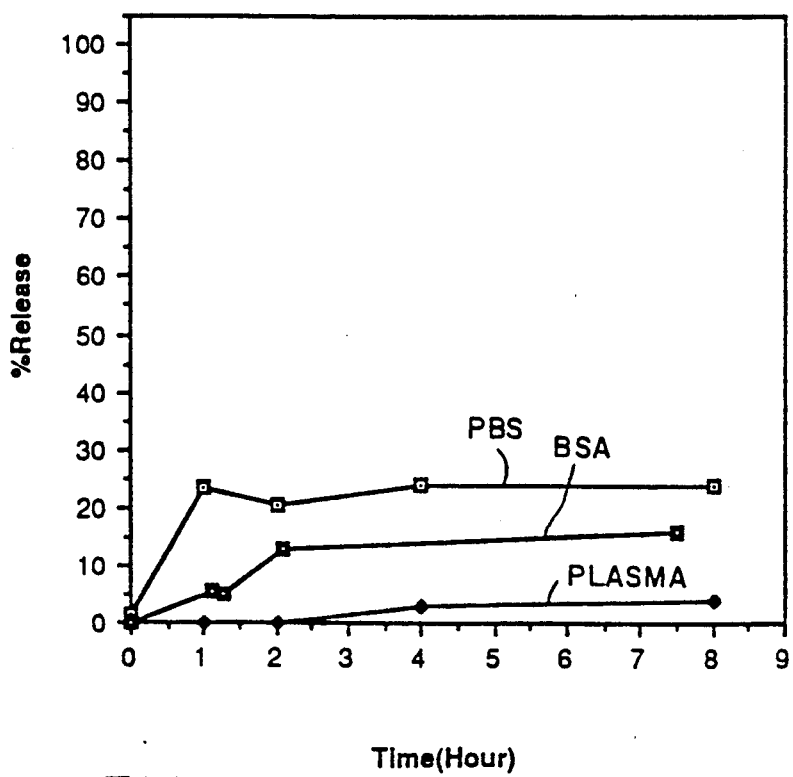

FIG. 4 illustrates the release of entrapped calcein from the plasma-treated, small unilamellar liposomes (d 105 nm) composed of DOPE:OA (2:1). Incubation was at 37° C. in the presence of PBS, 90% human plasma, or 0.5 mg/ml BSA.

Figure 5:
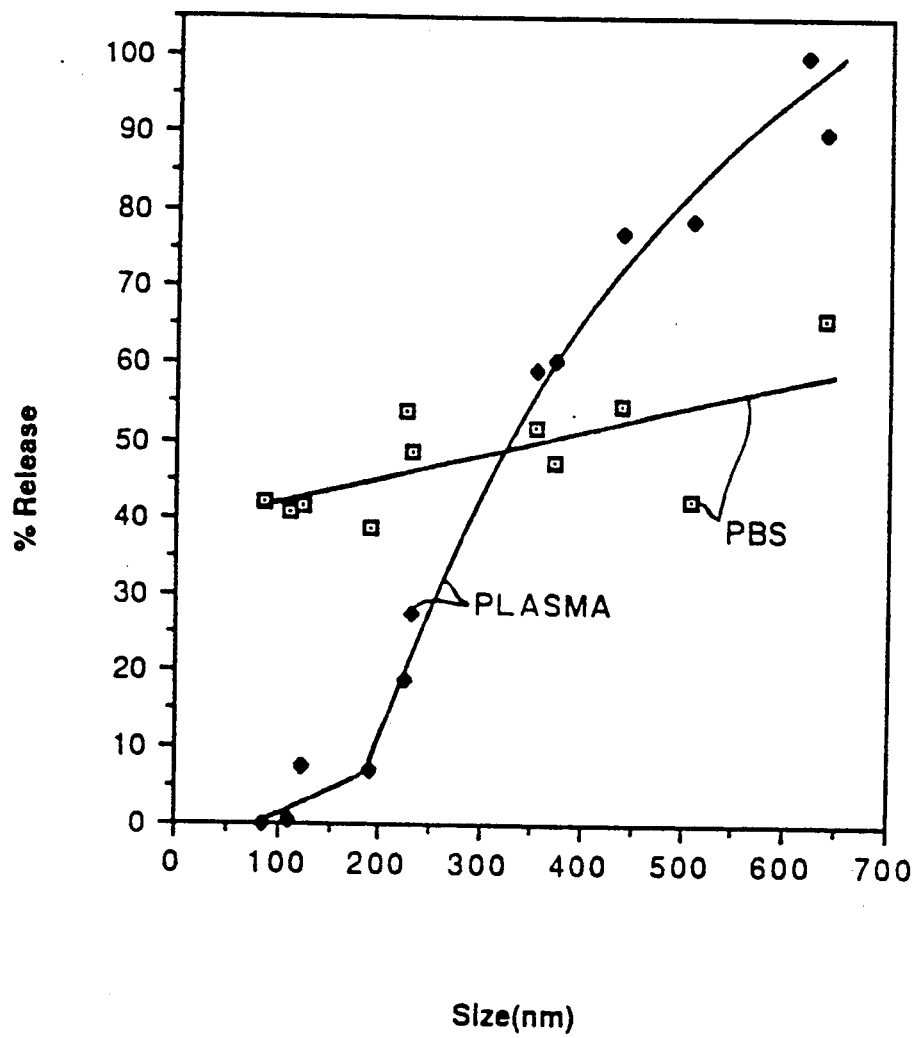

FIG. 5 shows that the plasma stabilization of liposome composed of DOPE:OA (2:1) is dependent on liposome size. Liposomes were prepared by the detergent-dialysis method and then extruded through the polycarbonate filter of defined pore size to obtain liposomes of variable diameter. Calcein release was measured in PBS, or 90% human plasma, after 4 hour incubation at 37° C.

DETAILED DESCRIPTION OF THE PREFERRED EMBODIMENTS

Figure 1:
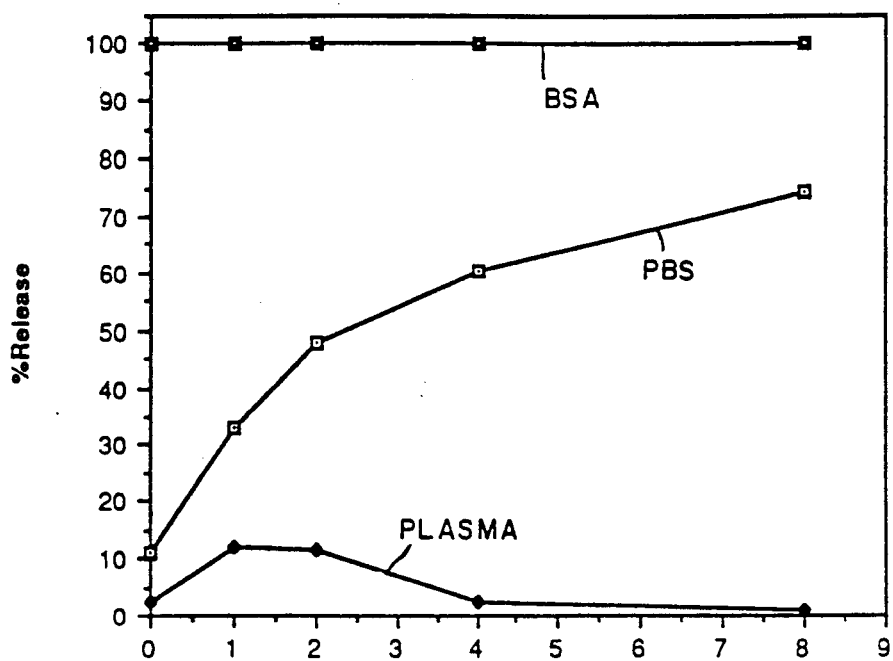
FIG. 1 illustrates the rate of release of entrapped calcein from the small unilamellar liposomes (d 105 nm) composed of DOPE:OA (2:1). Incubation was at 37° C. in the presence of PBS, 90% human plasma or 0.5 mg/ml BSA. BSA caused instant release of calcein from the liposomes.

Small unilamellar liposomes comprising DOPE and OA (2:1 mole ratio) are not stable when incubated at 37° C. in a protein-free, simple buffer such as the phosphate-buffered saline, pH 7.4. They spontaneously release the entrapped calcein, a fluorescent dye within a few hours of incubation, as shown in FIG. 1. The lysis of liposome can be accelerated by adding albumin to the liposome suspension (FIG. 1). Albumin lyses the liposomes by extracting the OA from the liposome, leaving the liposomes with an insufficient amount of OA for bilayer stability.

However, if a stabilizing amount of one or more micelle-forming amphiphiles are added to the freshly prepared small unilamellar liposomes comprising DOPE:OA (2:1), the liposomes become stable upon subsequent challenge by albumin. FIG. 2 shows an example using the micelle-forming amphiphile, $GM_1$. $GM_1$ was mixed with the liposomes at various concentrations and incubated at 37° C. for 15 min. An aliquot of the mixture was then diluted to 2 ml PBS in a cuvette and the release of calcein was monitored fluorometrically with time (t=0 in FIG. 2). At t=2 min., bovine serum albumin (final conc. 0.44 mg/ml) was added to the cuvette to induce the liposome lysis. As can be seen, there was a dose-dependent liposome stabilization by the added $GM_1$. At a concentration of 4 ug/ml or above, $GM_1$ completely stabilized the liposome against the lytic action of BSA.

A series of amphiphiles have been tested following these initial observations including, lipids and proteins, for their ability to stabilize DOPE:OA liposomes using the above-described protocol. Table I shows the percent of calcein release before and 7 min. after the addition of BSA for liposomes preincubated 15 min at 37° C. with these amphiphiles at the indicated concentration.

TABLE I

Stabilization of Small Unilamellar Liposomes Comprising DOPE:OA (2:1) by Amphiphiles

| Amphiphile | Conc. (mg/ml) | % calcein release before BSA | % calcein release after BSA |
|---|---|---|---|
| None | — | 0 | 100 |
| $GM_1$ | 0.04 | 3.0 | −3.7 |
| GT1b | 0.8 | 0 | −0.8 |
| lysoPC | 0.8 | 0 | −0.1 |
| sulfatide | 0.8 | 23.2 | 34.6 |
| DOPC | 0.8 | 65.8 | 98.5 |
| sial-lac-DOPE | 0.8 | −0.6 | 4.1 |
| AraCDP-DG | 0.4 | 0.1 | −0.1 |
| glycophorin A | 0.8 | 0 | 0.6 |
| HDL | 0.8 | 3.2 | −0.9 |
| Cyt $b_5$ | 0.8 | 0 | 3.1 |

The small unilamellar liposomes (0.8 mg lipid/ml, average diameter 130–188 nm) with entrapped calcein were incubated with the amphiphiles at the indicated concentration for 15 min. at 37° C. An aliquot (10 ul) of the mixture was diluted to 2 ml PBS and the % calcein released was measured fluorometrically. BSA (final conc. 0.44 mg/ml) was then added and the % calcein release was again measured 7 min. later.

As shown in Table I, all amphiphiles tested, except DOPC, stabilized the liposome against the subsequent addition of BSA. DOPC, added as sonicated liposomes, did not stabilize the DOPE:OA liposomes. In fact, it caused a partial lysis of the liposomes during the 15 min. incubation. This is probably because DOPC liposomes can absorb OA from the DOPE:OA liposomes and cause the destabilization of the DOPE:OA liposomes. Amphiphile-stabilized liposomes are also stable in human plasma; less than 10% calcein release was observed after 4 hour incubation with 90% human plasma at 37° C.

The amphiphiles which showed stabilization activity readily form micelles in PBS. They represent a broad group of compounds with various biological and/or pharmacological activity. $GM_1$, GT1b and sulfatide are glycolipids which contain negatively charged group (sialic acid or sulfate). They are structural lipids of the cell surface membrane and $GM_1$ has been identified as the receptor for cholera toxin. Lyso-PC is a metabolite of PC. Sial-lact-DOPE is a synthetic glycophospholipid. AraCDP-DG is an anticancer drug. Amphipathic proteins such as cytochrome $b_5$ are known to insert into the lipid bilayer. HDL is a blood lipoprotein which is known to interact with liposomes.

Without wishing to be bound by conjecture, it is believed that the stabilization activity of the amphiphiles is due to the insertion of apoliproprotein(s) (such as $A_1$) into the liposome bilayer.

The stabilization activity of HDL was further compared with other classes of human lipoprotein. As can be seen in FIG. 3, HDL (high density lipoprotein) showed the most potent stabilization activity followed by VLDL (very low density lipoprotein) and then LDL (low density). As little as 2 ug/ml HDL completely stabilized the DOPE:OA liposomes. This is to be compared with the HDL concentration in normal human blood, which is about 3.6 mg/ml. Furthermore, the experiments shown in FIG. 3 were done by adding the lipoproteins and BSA at the same time, i.e., the stabilizer and the lytic agent were present at the same time to simulate the normal blood situation (i.e., simulate in vivo conditions). Even when tested concurrently with BSA, HDL rapidly and potently stabilized the liposomes against the lytic action of BSA.

Since HDL is quite abundant in human plasma or serum, DOPE:OA liposomes were also tested without going through the above-described stabilization procedure. That is, they were studied for their stability when directly exposed to human plasma. As can be seen in FIG. 1, although the liposome is quite unstable in PBS, they are remarkably stable in 90% human plasma. Liposomes preincubated in 50% plasma for 1 hour at 37° C. can be isolated from the excess plasma component by gel filtration on a Bio-Gel A 0.5M column. The plasma-treated liposomes are now very stable upon incubation at 37° C. in either PBS, BSA or 90% plasma (FIG. 4). This is to be compared with the untreated liposomes which are not stable in PBS or BSA (FIG. 1). The stabilized liposomes are stable upon storage at 4° C. or 25° C. in PBS for at least about 4 months.

It is believed that the HDL in the plasma or serum must have rapidly stabilized these liposomes against the lytic activity of the albumin which is also in the same plasma.

According to the above results, it is envisioned that freshly prepared small unilamellar liposomes comprising DOPE:OA, and encapsulating a drug or combination of drugs, can be stabilized by the patient's own serum or plasma prepared ahead of time, and then injected into that same patient as a method of therapy. This procedure will greatly reduce the chance of cross-contamination and cross-reaction of the patient with blood products from other individuals.

It is interesting to note that the plasma or serum stabilization of the DOPE:OA liposomes is liposome size-dependent. Larger liposomes (d>600 nm) were prepared by the detergent-dialysis method and extruded through polycarbonate filters of defined pore size and the average particle diameter of the extruded liposomes was determined by dynamic laser light scattering using a Coulter N4SD particle-size counter.

Liposomes of different size were tested for calcein release in PBS and 90% plasma (4 hours at 37° C.) and the results are shown in FIG. 5. The stability of liposomes in PBS was not very dependent on the liposome size; larger liposomes released only slightly more calcein than the smaller ones. However, the dye release from liposomes incubated in plasma was a sensitive function of the liposome size. Small liposomes (d<200 nm) released only 10% calcein in 4 hours, whereas large liposomes (d>600 nm) released almost all of the entrapped dye during the same period of incubation. Large liposomes were more stable in PBS than in plasma. Small liposomes showed the opposite behavior, i.e., they were more stable in plasma than in PBS. Thus, liposome size determines the extent of liposome stabilization; only small liposomes can be stabilized by plasma.

The liposome stabilization compositions and procedures disclosed here are commercially significant for the following reasons:

1. The liposomes are stable for storage in a simple buffer at 4° C. or room temperature for prolonged periods of time.
2. The liposomes are stable in the blood without leaking the entrapped contents.
3. Many amphiphiles can be used to stabilize the liposomes including drugs (araCDP-DG), receptors (GM$_1$) and proteins. The pharmacological activity of the liposome can be easily modified with the method.
4. The procedure does not require the exposure of the stabilizer to harsh conditions such as sonication, organic solvent, etc.
5. The liposomes can be stabilized by the patient's own plasma or serum for truly individualized therapy.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

LIST OF ABBREVIATIONS

The following abbreviations are used throughout this disclosure, particularly in the examples which follow:
PE: phosphatidylethanolamine
DOPE: dioleoyl phosphatidylethanolamine
OA: oleic acid
PC: phosphatidylcholine
HDL: high density lipoprotein
LDL: low density lipoprotein
VLDL: very low density lipoprotein
Lyso-PC: lysophosphatidylcholine
Cyt b$_5$: cytochrome b$_5$
AraCDP-DG: cytosine arabinoside diphosphate diacylglycerol
Sial-lac-DOPE: N-(sialolactosyl)dioleoyl phosphatidylethanolamine
EGTA: ethylene bis (oxyethylenenitrilo) tetraacetic acid
PBS: phosphate buffered saline
BSA: bovine serum albumin

MATERIALS

DOPE and lyso-PC (2-palmitoyl lysophosphatidylcholine) were purchased from Avanti Polar lipids. OA, sulfatide, glycophorin A and calcein were obtained from Sigma Chemical Co. Gangliosides (GM$_1$, GT1b) were obtained from Calbiochem. Cytochrome b$_5$ and human lipoproteins (HDL, LDL, VLDL) were obtained from Dr. Peter Holloway and Dr. Jere Segrest, respectively. AraCDP-DG was obtained from Dr. Joseph Turcotte. Sial-lac-DOPE way synthesized by a reductive amination reaction of sialolactose and DOPE using NaCNBH$_3$.

EXAMPLE 1

Preparation of small unilamellar liposomes:

10 umole of lipid containing DOPE (6.67 umole) and OA (3.33 umole) was dried with a gentle stream of N$_2$ gas. The dry lipids were kept under vacuum for a minimum of 30 min. and they hydrated for at least 5 hours at room temperature in 1 ml of PBS (160 mM NaCl, 3.2 mM KCl, 1.8 mM KH$_2$PO$_4$, 0.12 mM NA$_2$HPO$_4$, pH 8.0) containing 50 mM calcein, 0.55 mM EGTA at pH 8.0. The osmolarity of this buffer was adjusted to that of human plasma with 10% PBS. Trace amount of [$^3$H]cholestanyl ether was included to monitor the lipids.

The lipid suspension was sonicated with a bath sonicator (Laboratory Supplies, Hicksville, N.Y.) and the pH was adjusted and maintained at 8.0 during sonication. The liposome suspension was left for 2 hours at room temperature to facilitate the annealing process. Free calcein was separated from liposome by using Bio-Gel A-0.5m column chromatography equilibrated with PBS which was adjusted to be isotonic to the calcein containing buffer. The size (diameter) of the liposome was measured by dynamic laser light scattering using a Coulter N3SD instrument.

EXAMPLE 2

Preparation of large liposomes of various diameters:

Large unilamellar vesicles were prepared by a detergent dialysis method. 10 umol of lipid was dried with a gentle stream of $N_2$ gas. The dry lipid was kept under vacuum for a minimum of 30 min. and suspended in 900 ul of PBS buffer containing 50 mM calcein and 0.55 mM EGTA which was isotonic to human plasma. [$^3$H] cholestanyl ether was included in the lipid mixture to monitor the lipids. The lipid suspension was sonicated with a bath sonicator (Laboratory Supplies, Hicksville, N.Y.) and the pH was adjusted to pH 8.0. 100 ul of octylglucoside (100 umol) was added. The mixture was vortexed and dialyzed at room temperature against 100 ml of the buffer used above containing 1 g of washed SM-2 beads for 48 hours with slow stirring. The liposomes were extruded through the polycarbonate filters of defined pore size (manufactured by Nucleopore Corp.) to obtain large unilamellar liposomes of defined size. The free calcein was then removed by gel filtration on Bio-Gel A-0.5M column as above. The size of the liposomes was measured by dynamic laser light scattering as above.

EXAMPLE 3

Liposome stabilization assay

A liposome suspension prewarmed to 37° C. containing 80 ug of lipid was incubated with 8 ug amphiphile in 100 ul PBS for 15 min. 10 ul of the mixture was added into a cuvette containing 1.99 ml PBS for fluorescence measurement with constant stirring. 10 ul BSA (88 mg/ml) was added after 2 min. incubation in the cuvette. The fluorescent intensity was measured with excitation wavelength of 490 nm and emission wavelength of 520 nm. The total fluorescent intensity was obtained by adding 50 ul deoxycholate (5%) to lyse the liposomes. Release of the entrapped calcein from the liposomes was calculated with the following equation:

$$\% \text{ Release} = \frac{(Ft/F) Fx - Fo}{Ft - Fo} \quad (\text{eq. 1})$$

where Fo is the fluorescence intensity of the liposomes in the absence of any additive. Ft is the total fluorescence intensity after addition of deoxycholate to the liposomes in the absence of the additive to release all of the entrapped calcine. Fx is the fluorescence intensity of the liposome in the presence of the additive at time=x. F is the total fluorescence intensity of the liposomes in the presence of the additive by adding deoxycholate to release all of the entrapped calcein. The additives used in this series of experiments wee the amphiphiles listed in Table 1.

EXAMPLE 4

Comparison of stabilization effect among different classes of human lipoprotein 10 ul of liposomes containing 6 to 8 ug of lipids was added to a cuvette containing 1.99 ml PBS with BSA (0.5 mg/ml) and different concentrations of lipoprotein. The calcein release was measured and calculated with eq. 1 as described above. Fx was obtained at 9 min. after the incubation.

EXAMPLE 5

Stability assay of the amphiphile stabilized DOPE:OA liposome in 90% human plasma Amphiphile-stabilized liposomes were obtained by incubating the liposomes with the amphiphile (lipid:amphiphile=10:1 (w/w)) for 30 min. at 37° C. The stabilized liposomes were diluted 10-fold with human plasma and incubated at 37° C. for different periods of time. 10 ul of the mixture was diluted to 2 ml PBS to measure for calcein release fluorometrically.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of stabilizing freshly prepared, small, unilamellar liposomes in blood or body fluids, said liposomes consisting essentially of an unsaturated phosphatidylethanolamine and a fatty acid as the major components of the liposome preparation, which comprises adding a blood or body fluid stabilizing amount of a micelle-forming amphiphile to a suspension of said liposomes.

2. The method of claim 1, wherein the unsaturated phosphatidylethanolamine in the liposome preparation is dioleoyl phosphatidylethanolamine.

3. The method of claim 2, wherein the fatty acid in the liposome preparation is oleic acid.

4. The method of claim 3, wherein the ratio of dioleoyl phosphatidylethanolamine to oleic acid in the liposome preparation is from about 10:1 to 1:10.

5. The method of claim 3, wherein the ratio of dioleoyl phosphatidylethanolamine to oleic acid in the liposome preparation is from about 5:1 to 1:5.

6. The method of claim 3, wherein the ratio of dioleoyl phosphatidylethanolamine to oleic acid in the liposome preparation is from about 2:1 to 1:2.

7. The method of claim 1, wherein the micelle-forming amphiphile is selected from the group consisting of micelle-forming lysophospholipids, gangliosides, sulfatide, synthetic glycophospholipids, lipophilic drugs, and amphipathic proteins 8. The method of claim 7, wherein the ganglioside is selected from the group consisting of $GM_1$ and GTlb.

9. The method of claim 7, wherein the synthetic glycophospholipid is sialolactosylphosphatidylethanolamine.

10. The method of claim 7, wherein the lipophilic drug is cytosine arabinoside diphosphate diacyglycerol.

11. The method of claim 7, wherein the amphipathic proteins are selected from the group consisting of cytochrome $b_5$, human high density lipoprotein (HDL), human low density lipoprotein (LDL), human very low density lipoprotein (VLDL), and human glycophorin A.

12. A method of stabilizing freshly prepared, small, unilamellar liposomes in blood or other body fluids, said liposomes consisting essentially of an unsaturated phosphatidylethanolamine and a fatty acid as the major components of the liposome preparation, which comprises mixing said liposomes with a stabilizing amount of human plasma, serum or whole blood.

13. The method of claim 12, wherein the unsaturated phosphatidylethanolamine in the liposome preparation is dioleoyl phosphatidylethanolamine.

14. The method of claim 13, wherein the fatty acid in the liposome preparation is oleic acid.

15. The method of claim 14, wherein the ratio of dioleoyl phosphatidylethanolamine to oleic acid in the liposome preparation is from about 10:1 to 1:10.

16. The method of claim 14, wherein the ratio of dioleoyl phosphatidylethanolamine to oleic acid in the liposome preparation is from about 5:1 to 1:5.

17. The method of claim 14, wherein the ratio of dioleoyl phosphatidylethanolamine to oleic acid in the liposome preparation is from about 2:1 to 1:2.

18. The method of claim 12, which further comprises purifying the stabilized liposomes by removing them from contact with said human plasma, serum, or whole blood.

19. Blood-stable, cholesterol-free liposomes prepared by the method of claim 1.

20. Blood-stable, cholesterol-free liposomes prepared by the method of claim 12.

21. A method of delivering one or more drugs to a mammalian patient so as to greatly reduce the chance of cross-contamination and cross-reaction of the blood of said patient with blood products from other sources, said method comprising the steps of:
   (a) freshly preparing small unilamellar liposomes consisting essentially of (2:1) DOPE:OA, said liposomes encapsulating the one or more drugs to be delivered to said patient;
   (b) stabilizing the freshly prepared liposomes by mixing said liposomes with a stabilizing amount of the patient's own blood, serum or plasma; and
   (c) injecting into the patient, an effective amount of the drug containing stabilized liposomes.

22. The method of claim 21, wherein the stabilizing amount of the patient'blood, serum, or plasma is about 50% by weight.

* * * * *